US007658338B2

(12) United States Patent
Matsumoto et al.

(10) Patent No.: US 7,658,338 B2
(45) Date of Patent: Feb. 9, 2010

(54) SMALL FIXED QUANTITY DISPENSER FOR AEROSOL CONTAINER

(75) Inventors: Keiko Matsumoto, Tokyo (JP); Ken Ogata, Moroyama-machi (JP)

(73) Assignees: Taisho Pharmaceutical Co., Ltd., Tokyo (JP); Toyo Aerosol Industry Co., Ltd., Tokyo (JP)

( * ) Notice: Subject to any disclaimer, the term of this patent is extended or adjusted under 35 U.S.C. 154(b) by 621 days.

(21) Appl. No.: 10/582,299

(22) PCT Filed: Nov. 15, 2004

(86) PCT No.: PCT/JP2004/016952

§ 371 (c)(1), (2), (4) Date: Jul. 19, 2006

(87) PCT Pub. No.: WO2005/056428

PCT Pub. Date: Jun. 23, 2005

(65) Prior Publication Data

US 2008/0312612 A1 Dec. 18, 2008

(30) Foreign Application Priority Data

Dec. 12, 2003 (JP) ............................ 2003-415569
Sep. 6, 2004 (JP) ............................ 2004-257953

(51) Int. Cl.
*B65D 83/20* (2006.01)
*B65D 83/16* (2006.01)
*B65D 83/14* (2006.01)
*B65D 83/28* (2006.01)
*B65D 83/52* (2006.01)
*B05B 7/32* (2006.01)
*A61M 11/00* (2006.01)

(52) U.S. Cl. ............... 239/337; 222/402.1; 222/402.13; 222/402.2; 128/200.23

(58) Field of Classification Search ................. 239/302, 239/337; 222/394, 402.1, 402.13, 402.2, 222/402.23; 128/200.14, 200.23; 604/289
See application file for complete search history.

(56) References Cited

U.S. PATENT DOCUMENTS 3,117,700 A * 1/1964 Gorman ................... 222/402.2

(Continued)

FOREIGN PATENT DOCUMENTS

JP 59-199468 11/1984

(Continued)

*Primary Examiner*—Darren W Gorman
(74) *Attorney, Agent, or Firm*—Jordan and Hamburg LLP

(57) ABSTRACT

A subdivided fixed amount distributing apparatus for aerosol containers is provided in which aerosol contents exceeding a specified amount is prevented from being used in one cycle by keeping constant in total number of injection times at all times. A structure is simplified by making it possible to eject total amount to the outside every one time by means of a fixed amount injection valve, so that damage to the distributing apparatus due to outside air temperature is prevented and movement of the distributing apparatus is made smooth when it is pushed and released. The subdivided fixed amount distributing apparatus includes a lower sleeve 18 secured to an upper end of an aerosol container 1, a nozzle body 15 formed with a nozzle 16 communicating with a stem 4, a rotating body 23 disposed in a rotatable manner with respect to the nozzle body 15 and the lower sleeve 18, an annular body 34 disposed at an upper side of the rotating body 23, a pushing body 45 pushing the stem 4, and an upper sleeve 37 secured to the lower sleeve 18 at a lower end thereof, in which pushing operation of the stem 4 enables a fixed amount injection of the aerosol contents and positional movement of a fitting piece 28 while pushing operation of the stem 4 and positional movement in the same direction of the fitting piece 28 are disabled by hitting the fitting piece 28 on an upper end surface of a lower projection 21 after positional movement by pushing operation of predetermined times.

3 Claims, 10 Drawing Sheets

U.S. PATENT DOCUMENTS 3,341,082 A * 9/1967 Meshberg .................. 222/148
4,565,302 A * 1/1986 Pfeiffer et al. ................ 222/38
5,775,321 A * 7/1998 Alband .................. 128/200.23
6,082,358 A * 7/2000 Scarrott et al. ......... 128/205.23
6,328,037 B1 * 12/2001 Scarrott et al. ......... 128/205.23
2003/0136802 A1 * 7/2003 Di Giovanni et al. .... 222/402.1

FOREIGN PATENT DOCUMENTS

JP 2001-232249 8/2001
JP 2002-513664 5/2002

* cited by examiner

SMALL FIXED QUANTITY DISPENSER FOR AEROSOL CONTAINER

TECHNICAL FIELD

This invention relates to a subdivided fixed amount distributing apparatus for aerosol containers allowing only use of a fixed amount of aerosol contents such as medical products, hair care products, and cosmetic products in which a use amount for one cycle, such as e.g., one day, several days, or one week, is restricted.

BACKGROUND TECHNOLOGY

Some aerosol contents contained in an aerosol container, such as medical products, hair care products, and cosmetic products may be used directly for human bodies. If such aerosol contents are used exceedingly in an amount more than a prescribed use amount, however, such use may cause harmful effects on human beings, or may result in wasteful use. As disclosed in Japanese Unexamined Patent Publication No. 2001-232249, a subdivided amount distributing apparatus for aerosol containers has been developed in which the apparatus capable of spraying a prescribed fixed amount usable in a certain period multiple times is connected to a stem of an aerosol container and disposed at an exterior of the aerosol container.

This subdivided amount distributing apparatus for aerosol containers is formed with a fixed amount chamber and a fixed amount injection valve, respectively, in the apparatus, and the aerosol contents of a fixed amount are introduced from the aerosol container main body into the fixed amount chamber and stored therein. The interior of the fixed amount chamber is normally pressurized with a piston, and the aerosol contents contained in the fixed amount chamber are injected multiple times in a subdivided manner through the fixed amount injection valve. Fixed amount injection during a prescribed period is allowed by injection of a fixed amount one or more times, thereby bringing advantages realizing distribution of aerosol contents suitable for medical products, hair products, and cosmetic products, which are otherwise not favorable when used in an amount of a prescribed amount or more or used in a wasteful manner.

SUMMARY OF THE INVENTION

Problems to be Solved by the Invention

However, the subdivided amount distributing apparatus described in Japanese Unexamined Patent Publication No. 2001-232249 is disposed at an exterior of the aerosol container. Therefore, the prescribed amounts in proportion to one day or one week are stored in the fixed amount chamber in the prescribed period in a state that the aerosol contents are pressurized, so that the volume of the aerosol contents may be expanded due to changes of the outer temperature in some occasions, and so that the distributing apparatus disposed at the exterior of the aerosol container may be damaged. Because the contents are injected while the fixed amount chamber is pressurized by the piston, injection is made continuously upon gasification of liquid gas remaining at, e.g., a space between the piston and the fixed amount chamber even after the injection of the liquid portion of the aerosol contents is completed, thereby having a defect to inject only gasified gas. In addition, the fixed amount chamber and the fixed amount injection valve, both, are required to be built in the distributing apparatus, thereby rendering assembly of the apparatus complicated and manufacturing costs high.

This invention, to solve the above problems, does not have a large fixed amount chamber able to inject the contents plural times at an exterior of the aerosol container like the subdivided fixed amount distributing apparatus for aerosol containers, but the aerosol contents can be injected after filled in the fixed amount chamber provided in the aerosol container, so that the distributing apparatus is prevented from receiving damages due to changes of the external temperature, thereby allowing the aerosol container to be used stably for a long period of time by safe use of the aerosol container, and thereby reducing the manufacturing costs.

It is to be noted that the specification and claims describe the aerosol container based on a state where a bottom side thereof is positioned as the lower side, in a position such that the bottom side is set as a lower portion and a side opposite to the bottom side is set as an upper portion.

Means to be Solved by the Invention

In an aspect of the invention, a subdivided fixed amount distributing apparatus for aerosol container includes a lower sleeve secured to a top end of the aerosol container and formed with a center opening in a center thereof, a nozzle body disposed in the center opening of the lower sleeve and formed with a nozzle bar connectable to a stem, the nozzle body formed with a nozzle communicating with the stem, a rotating body disposed at an upper side of the nozzle body and penetrating slidably the nozzle bar in a penetration bar formed on a center of the rotating body, the rotating body disposed rotatably with respect to the nozzle body and the lower bar as urged in an upper direction by a coil spring wound around the nozzle body, an annular body disposed at an upper side of the rotating body upon penetration of the penetration bar of the rotating body in an annular opening formed in a center of the annular body, a pushing body disposed at an upper side of the annular body upon penetration of penetration bar in a penetration opening, the pushing body pushing the stem via the annular body, the rotating body, and the nozzle body according to pushing down operation to open a fixed amount injection valve disposed in the aerosol container thereby allowing injection of entire amounts of aerosol contents within the fixed amount injection valve, and an upper sleeve attaching to the pushing body slidably in an up and down direction at the penetration opening, the upper sleeve secured to the lower sleeve at a lower end thereof, in which plural receiving blades whose lower end surface forms a tapered portion tapered at one corner are arranged annularly at an inner surface of the upper sleeve via insertion intervals, in which a fitting piece formed as projecting at a lower side of an outer periphery of the rotating body is rendered insertable in the insertion intervals and is disposed as facing to such the lower end surface of the sending blade as forming the tapered portion at a side of a bottom surface wall of the annular body, in which the fitting piece is pushed lower than a lower end of the receiving blade along with the annular body to push the stem to enable the fixed amount of the aerosol contents to be injected where the pushing body is pushed, in which the fitting piece pushed lower is inserted in the insertion interval along with each of inclined surfaces of the sending blade of the annular body and the receiving blade of the upper sleeve so the fitting piece as to be able to positionally move in the same direction one time, and in which pushing operation of the stem and positional movement of the fitting piece in the same direction are disabled by hitting the fitting piece on an upper end surface of an under sleeve projection formed as projecting at an upper surface of the under sleeve after the positional movement of a predetermined times according to the pushing operation of the pushing body.

In this case, the pushing body may be provided with a projecting piece formed at a bottom surface thereof, contactable to a contact wall formed at a side of an outer periphery of the penetration bar of the rotating body, and wherein hitting between the fitting piece and the lower sleeve projection is releasable upon arbitrary rotation of the rotating body in association with manual rotation of the pushing body.

In this case, the pushing body may be formed with a pushing projection at an upper surface thereof to be in pressurized contact with a user.

ADVANTAGES OF THE INVENTION

This invention simplifies the mechanism to render the manufacturing costs inexpensive by enabling the whole amount of aerosol contents contained in a fixed amount chamber formed in the aerosol container main body to be injected to the exterior each time when pushing a pushing body. This invention also renders the aerosol container usable safely by preventing the distributing apparatus from receiving damages due to influences of external temperature. In addition, this invention enables the easy manufacturing of the aerosol container by simplifying the mechanism. This invention furthermore stabilizes movement of the distributing apparatus to render stable use of the aerosol container by enabling an annular body, a rotating body, and the pushing body to move stably in an up and down direction in association with pushing by the pushing body and releasing of the pushing.

This invention, with the simple safe stable mechanism, has an advantage to render the aerosol container usable safely for a long time by limiting number of times in series of injections for fixed amount at one cycle and by preventing the aerosol contents from being used in an amount more than the prescribed amount, where medical products, hair care products, cosmetic products, etc. which are not suitable for use of a prescribed amount or more, are used as aerosol contents.

As description of reference numbers: 1 aerosol container, 3 fixed amount injection valve, 4 stem, 14 nozzle bar, 15 nozzle body, 16 nozzle, 18 lower sleeve, 20 center opening, 21 lower sleeve projection, 22 coil spring, 23 rotating body 26 penetration bar, 27 contact wall, 28 fitting piece, 33 annular opening, 34 annular body, 35 bottom surface wall, 36 sending blade, 37 upper sleeve, 38 receiving blade, 41 insertion interval, 45 pushing body, 46 pushing projection, 47 bottom surface, 48 projecting piece, 51 penetration opening, 56 inclined surface, 63 lower end portion.

DESCRIPTION OF THE PREFERRED EMBODIMENTS

Figure 1:
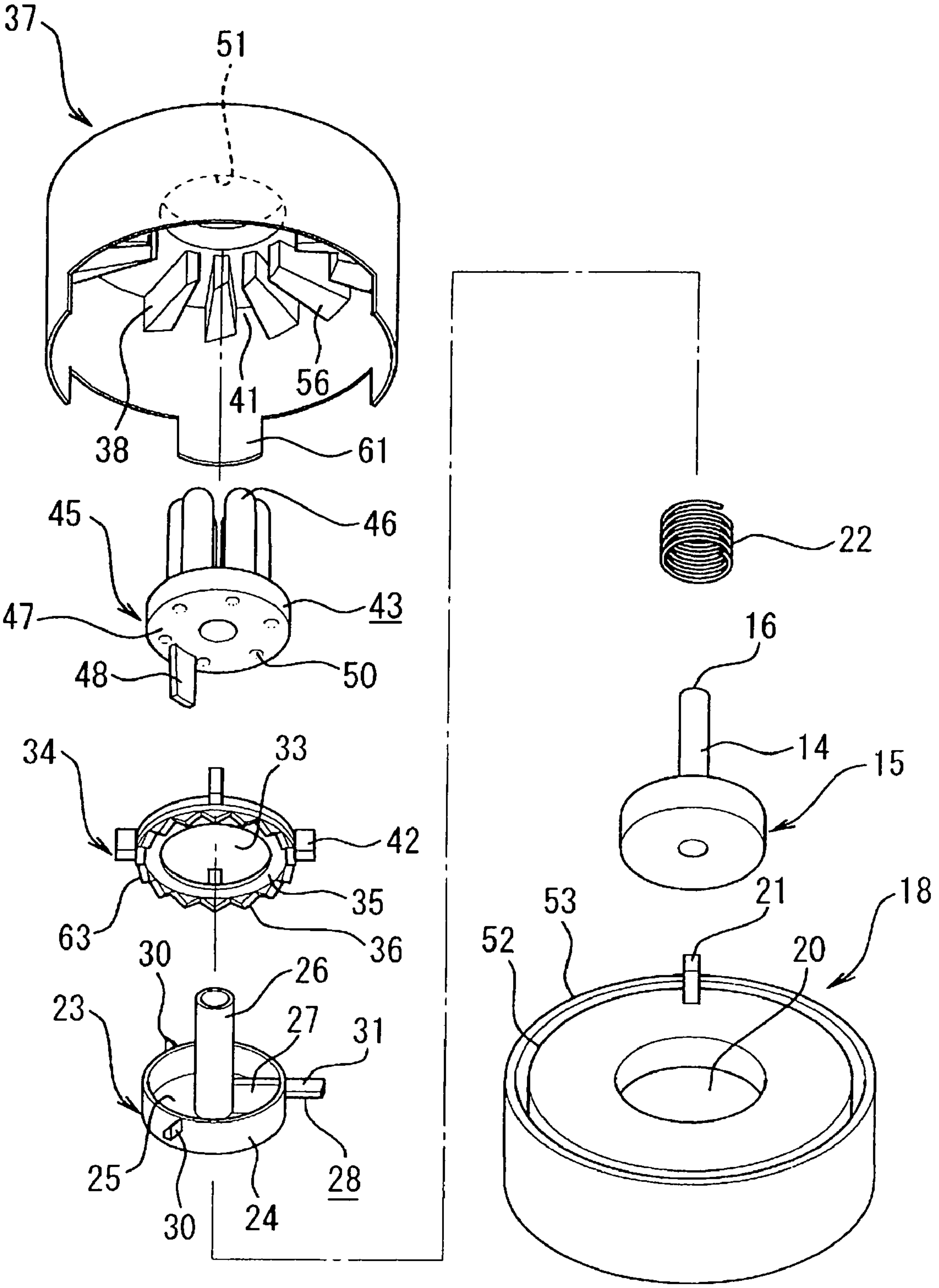
FIG. 1 is an exploded perspective view showing the first embodiment of the invention.
Figure 2:
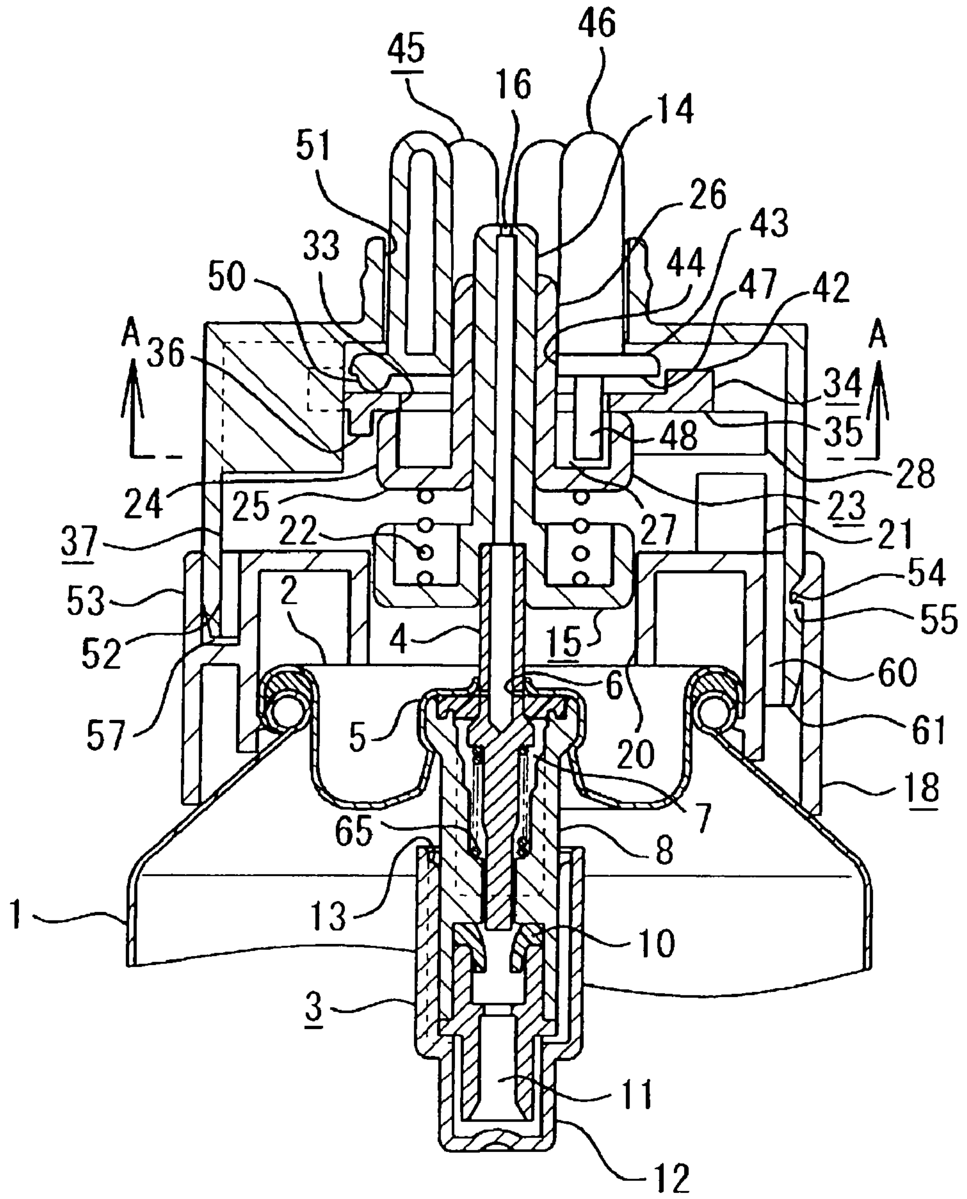
FIG. 2 is a cross section showing the first embodiment of the invention in an assembled state.

Referring to FIG. 1 through FIG. 10, a first embodiment using a hair growth agent injected plural times during one cycle use but subjecting to limitation of the whole use amount of injections during one cycle, is described hereinafter. Numeral 1 is an aerosol container made of aluminum, having an inner surface coated with polyamide-imide resin paint. As shown in FIG. 2, a fixed amount injection valve 3 whose top end is secured to a lid 2 is disposed in the aerosol container 1. A stem 4 disposed in the fixed amount injection valve 3 is formed penetrating a stem gasket 5 provided at an inner surface of the lid 2, and an orifice 6 is arranged on an outer side of the stem gasket 5 during a non-pushing state whereas the orifice 6 is arranged as inserted in a fixed amount chamber 7 during a pushing state. The orifice 6 communicates with an ejection route for the aerosol contents, formed at an upper end of the stem 4.

Figure 3:
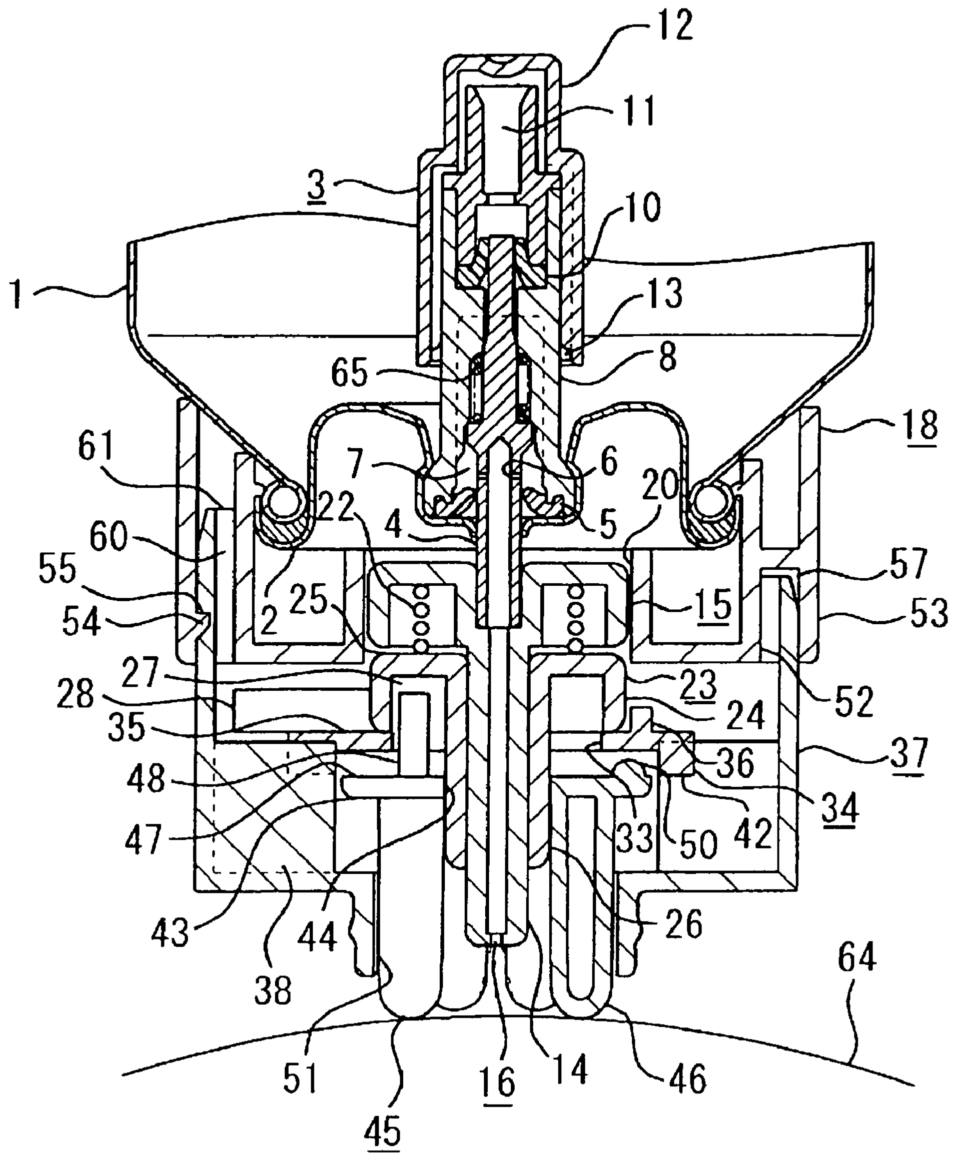
FIG. 3 is a cross section showing a fixed amount injection state.

The fixed amount injection valve 3 is formed with the fixed amount chamber 7 and a content introduction chamber 11 via an annular partition gasket 10 in a housing 8. The partition gasket 10 comes in close contact with the outer periphery of the stem 4 as shown in FIG. 3 to disconnect the fixed amount chamber 7 from the content introduction chamber 11, and the orifice 6 of the stem 4 is introduced into the interior of the fixed amount chamber 7 where the stem 4 is pushed and penetrated into the partition gasket 10 during use in a manner of up side down, so that the aerosol contents contained in the fixed amount chamber 7 only is discharged in the whole amount to the exterior through the ejection route of the stem 4. Upon release of pushing operation to the stem 4, as shown in FIG. 2, the stem 4 is returned to the original position to separate the partition gasket 10, thereby communicating the fixed amount chamber 7 with the content introduction chamber 11, and thereby introducing the aerosol contents contained in the content introduction chamber 11 into the fixed amount chamber 7.

The content introduction chamber 11 is normally in communication with an interior of the aerosol container 1 through an introduction route 13 provided between the outer periphery of the housing 8 and an outer sleeve 12 of the housing 8. It is to be noted that in this embodiment the fixed amount injection valve 3 thus formed is used but the structure is not limited as far as a fixed amount injection valve 3 used in other embodiments can inject the aerosol contents of a prescribed amount to the exterior by pushing operation of the stem 4 and is contained in the interior of the aerosol container 1.

As shown in FIG. 2, a nozzle body 15 projectingly forming an annular nozzle bar 14 is formed as connecting to the nozzle bar 14, thereby communicating a nozzle 16 formed at an upper end of the nozzle bar 14 with the ejection route of the stem 4. A lower sleeve 18 is secured to an upper end of the aerosol container 1 by rendering stem 4 connected to the nozzle body 15 through a center opening 20 formed in a center of the lower sleeve 18. This nozzle body 15 is disposed so as to be movable an up and down direction in the center opening 20 of the lower sleeve 18. As shown in FIG. 1, furthermore, one part of the lower sleeve 18 is projectingly formed as a lower sleeve projection 21 in an axial direction at an outer periphery side of the upper surface of the lower sleeve 18.

A rotating body 23 is disposed through a coil spring 22 onto an upper side of the nozzle body 15 thus disposed and is urged by the coil spring 22 in an upward direction. The rotating body 23 is formed by providing a cylindrical penetration bar 26 in an axial direction to a center of a base 25 having an annular wall 24 formed as projecting at an outer periphery thereof, and the nozzle bar 14 of the nozzle body 15 penetrates into the penetration bar 26.

The penetration bar 26 is formed to have an inner diameter thereof larger than an outer diameter of the nozzle bar 14 so as to be slidable in up, down, and peripheral directions along an outer periphery of the nozzle bar 14 in a case of penetration of the nozzle bar 14 into the penetration bar 26. The rotating body 23 is in a rotatably movable state independently from the nozzle body 15. As shown in FIG. 3, an outer diameter of the base 25 is set to smaller than a diameter of the center opening 20 of the lower sleeve 18 to allow the rotating body 23 to move in the center opening 20 of the lower sleeve 18.

As shown in FIG. 1, a contact wall 27 is formed between an outer circumferential surface of the penetration bar 26 and an inner circumferential surface of the annular wall 24 while a fitting piece 28 is formed on a flat surface flush with the contact wall 27 as projecting from an outer circumferential surface of the annular wall 24 to an exterior. On an outer circumference of the contact wall 24, two fitting short pieces 30 shorter than the outfitting piece 28 are formed other than the fitting piece 28 on the outer circumferential surface of the annular wall 24 as projecting in a manner that intervals between the fitting piece 28 and the two fitting short pieces 30 are equal to each other. Upper end surfaces of the fitting piece 28 and the two fitting short pieces 30 have tapered surfaces 31, 32 taped at one side in the same direction, respectively.

The annular body 34 provided with the annular opening at the center thereof is disposed on an upper side of the rotating body 23 such that the penetration bar 26 of the rotating body 23 is penetrated in the annular opening 33 and that a bottom surface wall 35 is in contact with the upper end surface of the annular wall 24 of the rotating body 34. As shown in FIG. 1, a plurality of blades 36 having a lower end as a tapered portion in a letter V shape are annularly formed in a projecting manner on an outer periphery of the bottom wall 35 of the annular body 34.

Figure 5:
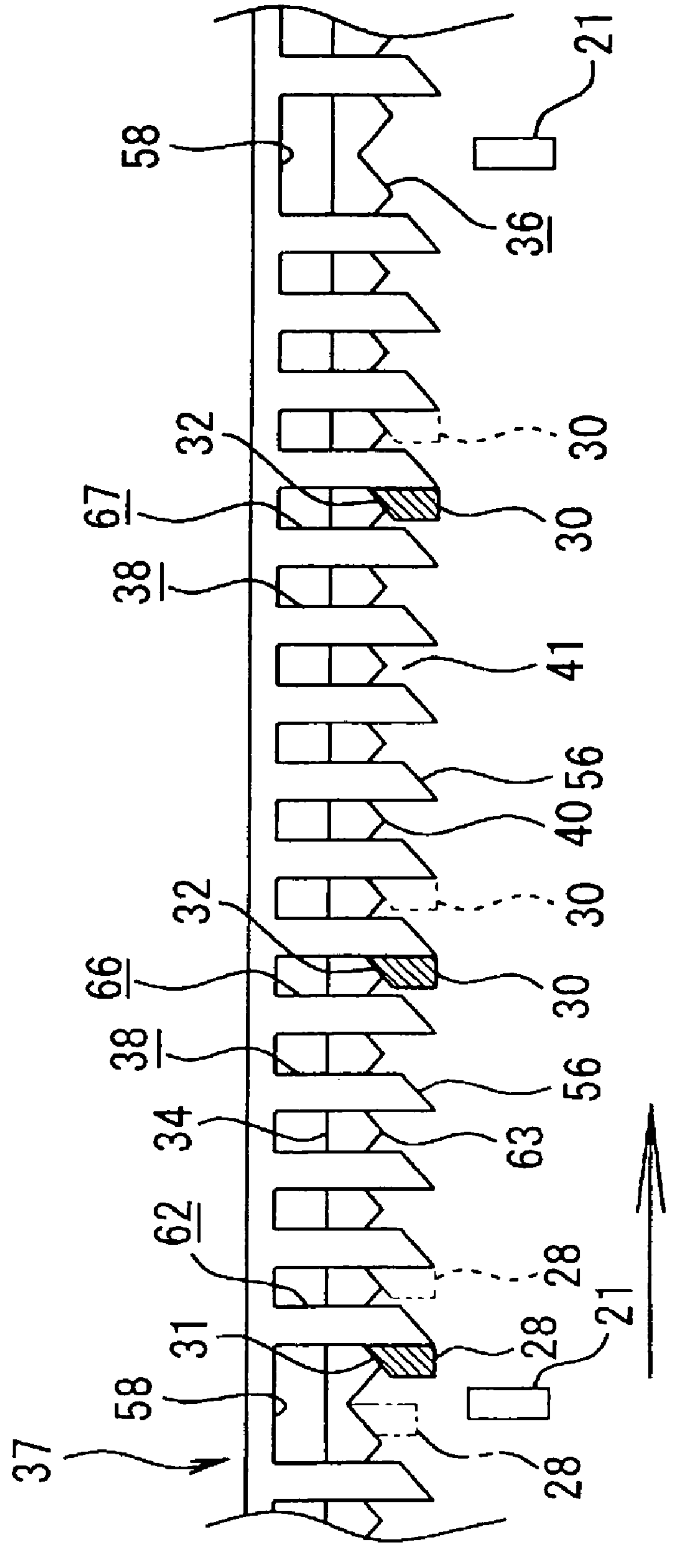
FIG. 5 is a conceptual view showing a state that the fitting piece and fitting short pieces are disposed at tapered surfaces of sending blades.
Figure 9:
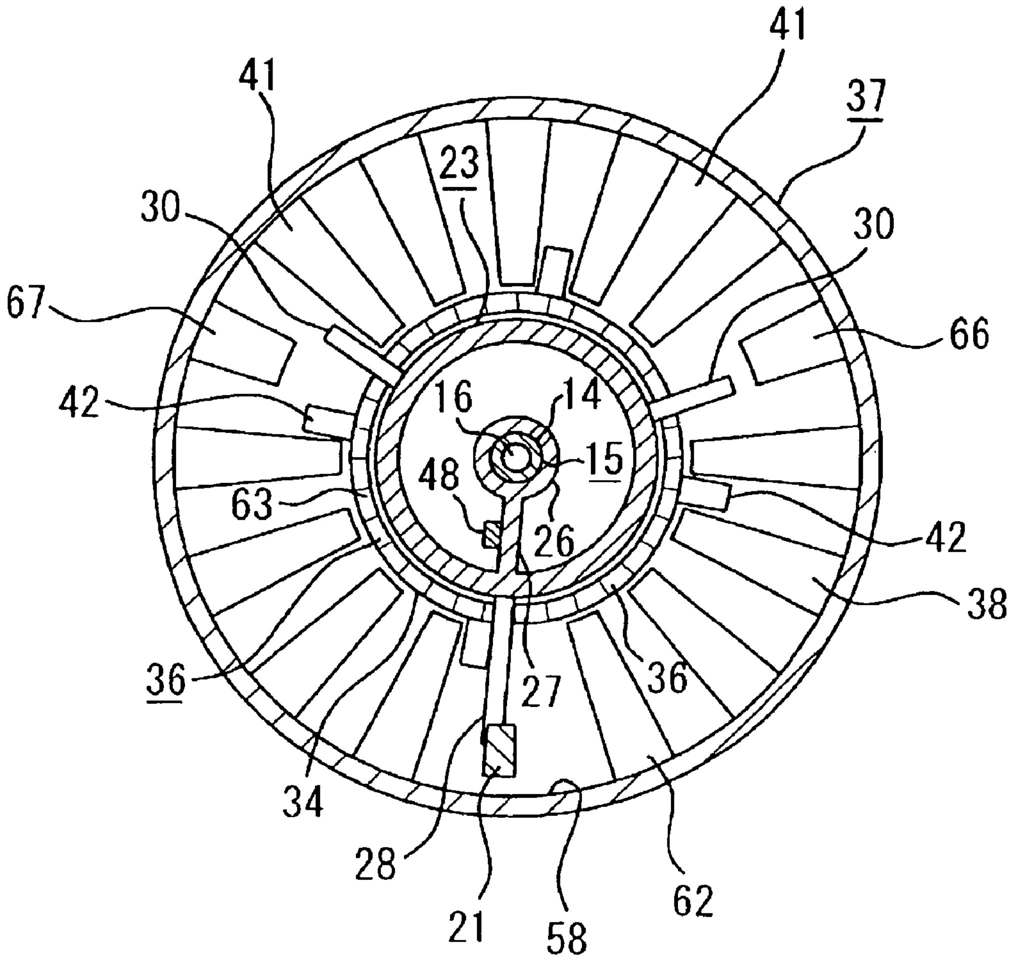
FIG. 9 is a cross section of FIG. 4 along the line B-B.

As shown in FIG. 9, the annular body 34 is formed in a manner that sending blades 36 are located at an axial center side with respect to receiving blades 38 of an upper sleeve 37 and a lower sleeve projection 21 of a lower sleeve 18 at the time of assembly. As shown in FIG. 5, the annular body 34 is also disposed in a manner that a vertex 40 on a projecting side of the sending blade 36 is located at an approximate center in an insertion interval 41 of the upper sleeve 37. Furthermore, as shown in FIG. 1, four outer peripheral projecting portions 42 are formed with equal intervals in a projecting manner on an outer periphery of an upper surface of the annular body 34.

A pushing body 45 in which the penetration bar 26 is penetrated in the penetration opening 44 formed in a center of a substrate 43 in a circular shape is disposed at an upper side of the annular body 34, and four bar-shaped pushing projections 46 having an arc-shaped front end are formed on an upper surface of the substrate 43 of the pushing body 45 as projecting in an axial direction. It is to be noted that the four pushing projections 46 in a shape as shown in FIG. 1 are formed in this embodiment but may be in any other shape capable of pushing a head of human being and the number of the pushing body is not especially limited.

A projecting piece 48 is formed on one location of a bottom surface 47 of the substrate 43 as projecting in a bottom-surface-axial direction. This projecting piece 48 is provided to rotate the rotating body 23 in a proceeding direction by putting the projecting piece 48 in contact with the contact wall 27 so that the fitting piece 28 is backed to an original position at the time of starting use of subsequent cycle after completion of use of one cycle. Other than the projecting piece 48, a plurality of bottom projections 50 in a semispheric shape are annularly formed on the bottom surface 47 of the substrate 43. The bottom projections 50 are provided to reduce frictional resistance which is caused between the annular body 34 and the pushing body 45 at the time of rotation of the pushing body 45.

As shown in FIG. 2, the pushing projections 46 of the pushing body 45 pierce through a piercing opening 51 of the upper sleeve 37. A lower end of the upper sleeve 37 is inserted in a space between an inner wall 52 and an outer wall 53 of the lower sleeve 18 to engage an engagement projection 54 formed on an inner circumferential surface of the outer wall 53 of the lower sleeve 18 with an engagement receiver 55 formed on an outer circumferential surface thereof so that the upper sleeve 37 is secured to the lower sleeve 18. The pushing projections 46 of the pushing body 45 are disposed as movable in an up and down direction dependently from the upper sleeve 37 while being urged by the coil spring 22 inside the piercing opening 51 of the upper sleeve 37 thus secured.

Furthermore, the receiving blades 38 having a lower end as an inclined surface 56 inclined at one side are formed as projecting in a bottom-end-axial direction on a ceiling surface of an inner wall of the upper sleeve 37, as shown in FIG. 1. This inclined surface 56 is formed in a direction opposite to the tapered surfaces 31, 32 of the fitting piece 28 and the fitting short pieces 30. As shown in FIG. 9, the fifteen receiving blades 38 of the upper sleeve 37 are continuously formed in an annular manner with insertion intervals 41 capable of fitting the fitting piece 28 and the fitting short pieces 30 of the rotating body 23 while a flat portion 58 at which the receiving blades 38 are not continuously formed is formed at one location of the upper sleeve 37.

The bottom wall surface 57 for connecting the inner wall 52 to the outer wall 53 is formed between the inner wall 52 and the outer wall 53 of the lower sleeve 18 while engagement recesses 60 are formed at three locations with equal intervals on the bottom wall surface 57. On the lower end of the upper sleeve 37, engagement convexes 61 are formed as projecting in an axial direction at three locations corresponding to the engagement recesses 60, respectively. The upper sleeve 37 is connected to the lower sleeve 18 in a rotatably immovable manner upon engagement of the engagement convexes 61 with the engagement recesses 60, so that the upper sleeve 37 and the lower sleeve 18 can be positioned to right locations. As shown in FIG. 5, it is therefore possible to easily dispose the flat portion 58 of the upper sleeve 37 on a location corresponding to the lower sleeve projection 21 of the lower sleeve 18.

With the structure thus described, to perform subdivide fixed amount distributing injection, the tapered surface 31 of the fitting piece 28 is first disposed at a lower end surface of the sending blade 36 in a state where a side surface of the fitting piece 28 in a proceeding direction as indicated by an arrow in full line shown in FIG. 5 is in contact with a side surface of a first receiving blade 62 before starting the subdivide fixed amount distributing injection. In the same manner, the two fitting short pieces 30 are respectively disposed at the lower end surfaces 63 of the sending blades 36. The aforementioned disposal is made by assembling the rotating body 23 and the annular body 34 at the time of manufacturing, in a manner to dispose the fitting piece 28 and the fitting short pieces 30 in the above manner. In this bout, the fixed amount chamber 7 and the content introduction chamber 11 formed at the fixed amount injection valve 3 are in a communicating state, as shown in FIG. 2, and a fixed amount of the aerosol contents is contained in the fixed amount chamber 7.

Next, the aerosol container 1 is made upside down, and as shown in FIG. 3, the pushing body 45 is pushed in a bottom direction of the aerosol container 1 in opposing to urging force of the coil spring 22 while rendering the pushing projections 46 of the pushing body 45 in contact with an injection target portion 64 such as a head of human being. At this time, this pushing operation of the pushing projections 46 can give massage effects to the injection target portion 64.

Figure 6:
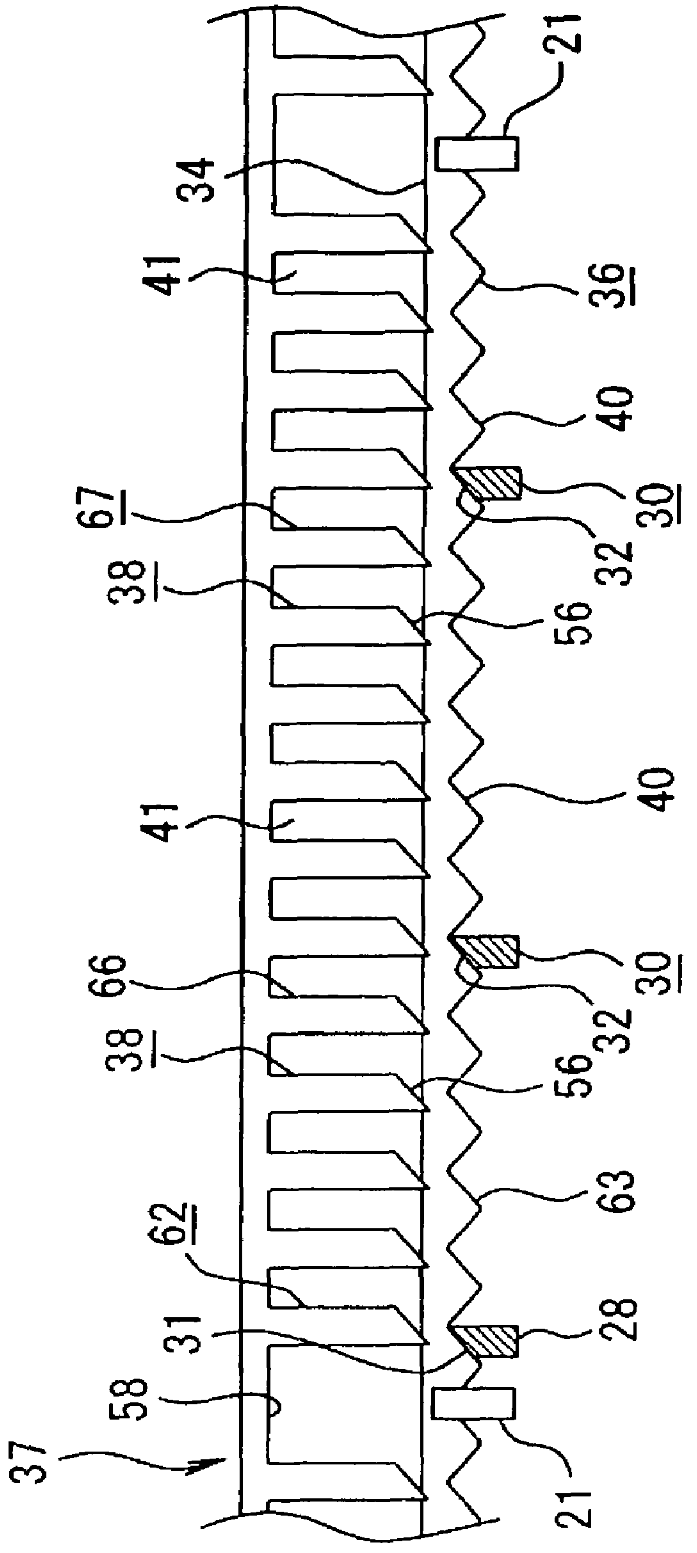
FIG. 6 is a conceptual view showing a state that the fitting piece and the fitting short pieces are pushed down along with the sending blades in a bottom direction.
Figure 7:
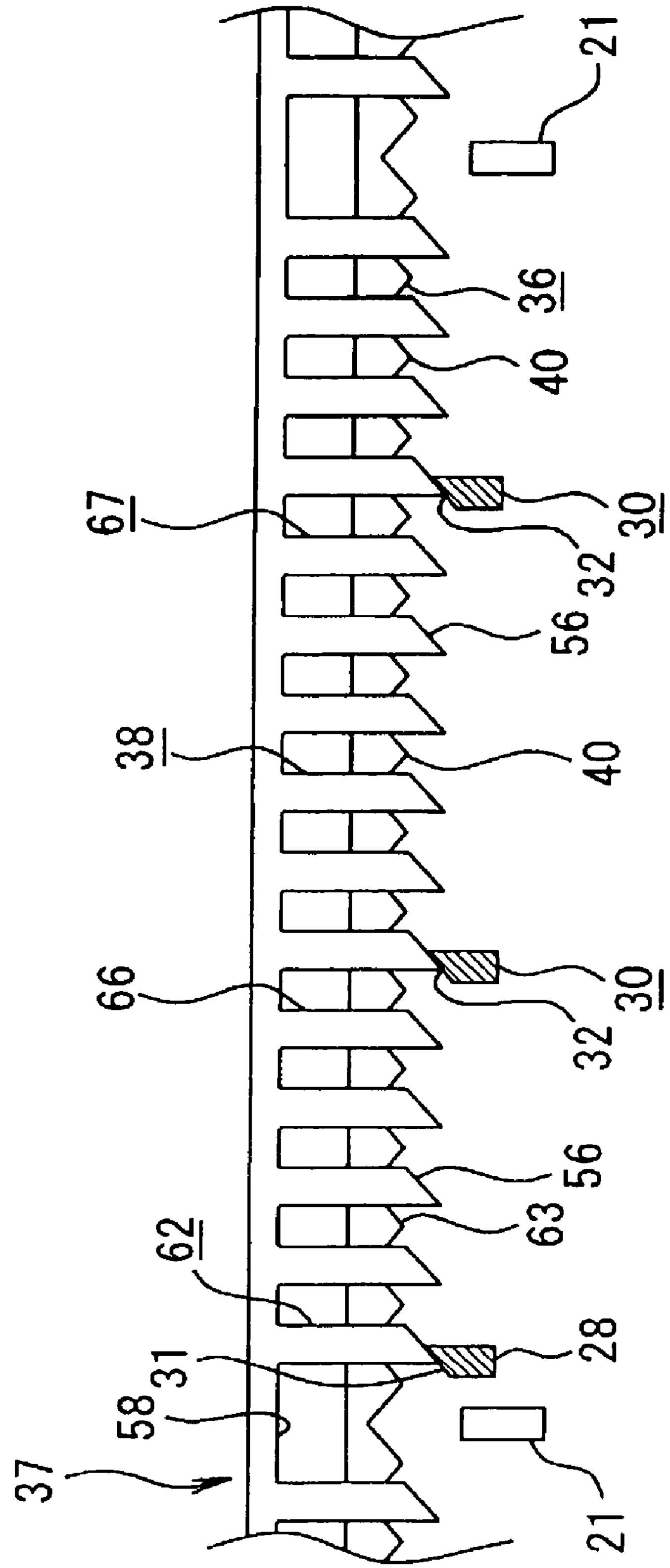
FIG. 7 is a conceptual view showing a state that upper end surfaces of the fitting piece and the fitting short pieces are in contact with lower end surfaces of receiving blades.

Since this pushing operation renders the annular body 34 move in a bottom direction, the fitting piece 28 and the fitting short pieces 30 disposed at the lower end surfaces 63 of the sending blades 36 of the annular body 34 move along with the sending blades 36, so that the sending blades 36, the fitting piece 28, and the fitting short pieces 30 move to a side of the bottom with respect to the receiving blades 38 at the time that the pushing body 45 is pushed up to the limit, as shown in FIG. 6.

At the same time, the nozzle body 15 and the stem 4 move toward the bottom of the aerosol container 1 as shown in FIG. 3. Therefore, the orifice 6 located on an outer side of the fixed amount chamber 7 during a non-pushing state is moved and disposed in an interior of the fixed amount chamber 7, thereby being put in contact with the aerosol contents inside the fixed amount chamber 7. Furthermore, the stem 4 pierces through the partition gasket 10 disposed between the content introduction chamber 11 and the fixed amount chamber 7, so that the outer periphery of the stem 4 comes in close contact with the partition gasket 10, thereby disconnecting the communication between the content introduction chamber 11 and the fixed chamber 7. Therefore, the whole amount of the aerosol contents contained in the fixed amount chamber 7 is injected out of the nozzle 16 through the orifice 4 and the introduction route of the stem 4.

When the pushing operation of the pushing body 25 is stopped after the whole amount of the aerosol contents contained in the fixed amount chamber 7 is injected, the pushing body 45 is moved by the urging force of the coil spring 22, in a direction opposite to the bottom of the aerosol container 1. The nozzle body 15 and the stem 4 are accordingly backed to the original positions by the urging force of the stem spring 65, and thus the orifice 6 is disposed at the outer side of the fixed amount chamber 7 again. Upon release of the pushing operation, the sending blades 36, the fitting piece 28, and the fitting short pieces 30 are moved in the same direction as the pushing body 45, by resilience of the coil spring 22 and the stem spring 65, so that the tapered surfaces 31, 32 of the fitting piece 28 and the fitting short pieces 30 hit, during moving operation, inclined surfaces 56 of the receiving blades 38, respectively, as shown in FIG. 2.

The fitting piece 28 and the fitting short pieces 30 slide into the insertion intervals 41 next to the insertion intervals 41 at which the fitting piece 28 and the fitting short pieces 30 were located before the pushing operation of the pushing body 45, while positionally moving in a proceeding direction along with the inclined surfaces 56 of the receiving blades 30, respectively. The fitting piece 28 and the fitting short pieces 30 are respectively disposed at the lower end surfaces 63 of the sending blades 36 arranged inside those insertion intervals 41, as indicated by a dashed line in FIG. 5. In this bout, since the two fitting short pieces 30 positionally moves in an up and down direction and in a proceeding direction at the same time along with the fitting piece 28, the rotating body 23 can be stably moved in a top and down axis direction while the substrate 25 of the rotating body 23 is kept in a horizontal position. Thus, the penetration bar 26 can be moved along the outer periphery of the nozzle bar 14 in an up and down direction smoothly during a pushing state and release of pushing state.

As shown in FIG. 9, the outer peripheral projecting portions 42 formed as projecting on the outer periphery of the annular body 34 are disposed as inserted between the upper sleeve 37 and the receiving blades 38, and move in an up and down direction along with the receiving blades 38 at both adjacent sides during a pushing state and release of pushing state, so that the annular body 34 moves in an up and down direction only and cannot move in a circumferential direction.

Upon release of pushing operation of the pushing body 45, the rotating body 23 positionally moves in a proceeding direction in association with movement of the fitting piece 28 while the annular body 34 moves in an up and down direction only independently from positional movement of the rotating body 23, so that the sending blades 36 of the annular body 34 can be stably moved at all times in an up and down direction at the time of positional movement of the fitting piece 28. The movement of the rotating body 23 and the annular body 34 thus described enable the distributing apparatus to be smoothly operated in injecting the fixed amount of the aerosol contents. With the steps described above, the fixed amount injection of the first time is completed. The substantially same steps are performed upon pushing operation of pushing body of the second time to inject the fixed amount of aerosol contents.

Figure 4:
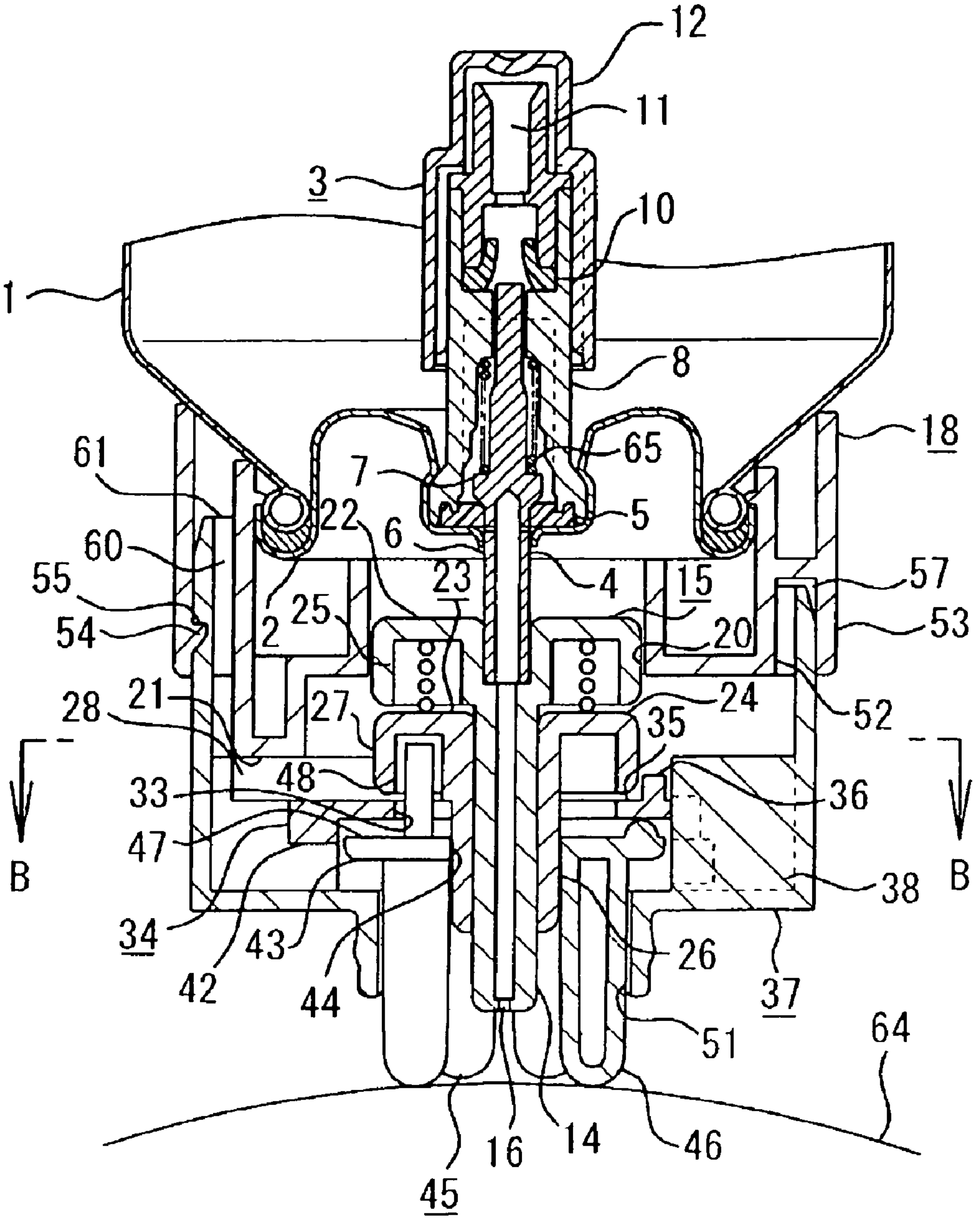
FIG. 4 is a cross section showing a state that a fitting piece hits a flat portion after completion of fixed amount injection for one cycle.

As described above, the fitting piece 28 moves sequentially between the insertion intervals 41 upon repeat of pushing and stop of pushing of the pushing body 45 at each time of the fixed amount injection. Where the pushing body 45 is further pushed after repeating the movement fifteen times in total, the fitting piece 28 slightly moves toward the bottom along with the sending blade 36 and thereafter hits the lower sleeve projection 21 formed as projecting on the lower sleeve 18, as shown in FIG. 4 and FIG. 8.

The nozzle body 15 and the stem 4 thus cannot be pushed any further toward the bottom of the aerosol container 1, and the fixed amount injection valve 3 is not opened in this state, so that the aerosol contents cannot be injected. At this point, use of the aerosol container 1 for one cycle is completed. Therefore, the aerosol contents cannot be injected even where the pushed body 45 is continuously pushed in such a state that use of one cycle is completed, so that the aerosol contents can be prevented from being used more than the prescribed amount.

Figure 8:
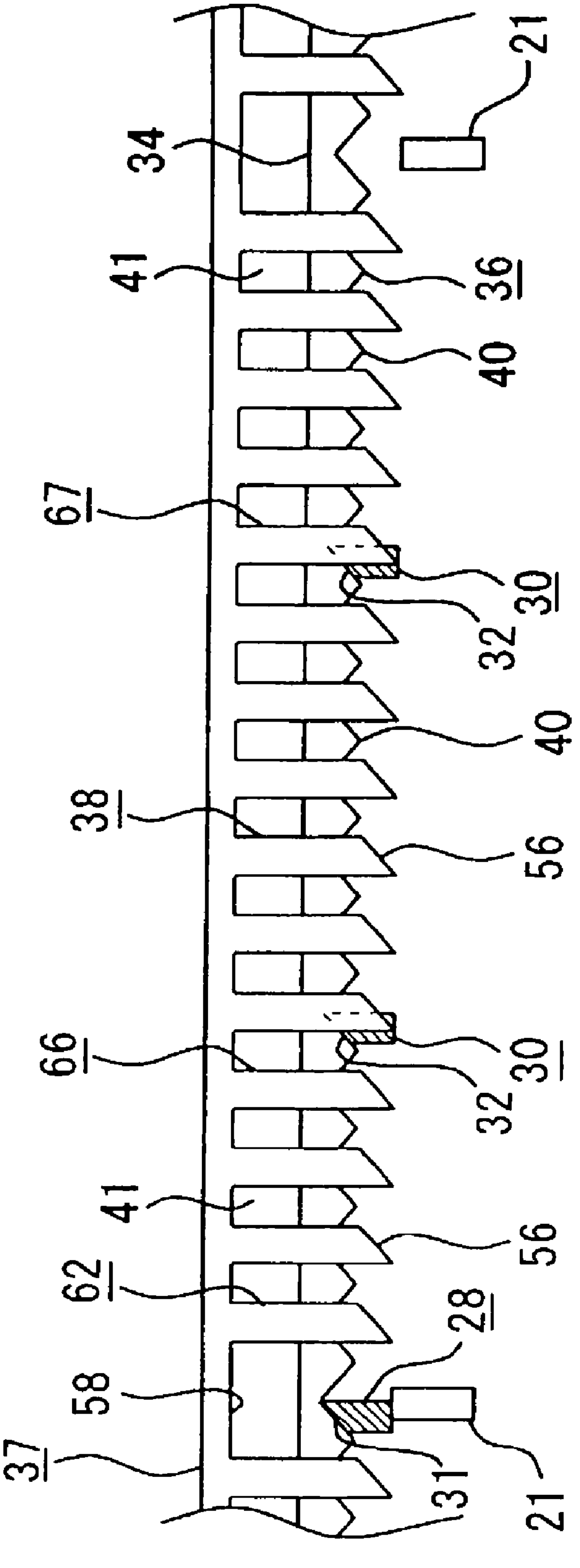
FIG. 8 is a conceptual view showing a state that the fitting piece hits the flat portion.

The next use cannot be subsequently started in a state where the use of one cycle is completed as describe above, and the fitting piece 28 hits the lower sleeve projection 21 as shown in FIG. 8, so that the rotating body 23 cannot be further rotated in a proceeding direction. Thus, the following steps are required to start the subsequent use of the next cycle. First, the pushing body 45 is rotated in a non-pushing state, until the projecting piece 48 of the pushing body 45 comes in contact with the contact wall 27 of the rotating body 23. Where the projecting piece 48 comes in contact with the contact wall 27 as shown in FIG. 9, the pushing body 45 is further rotated in the same direction in a state where the projecting piece 48 is in contact with the contact wall 27.

Figure 10:
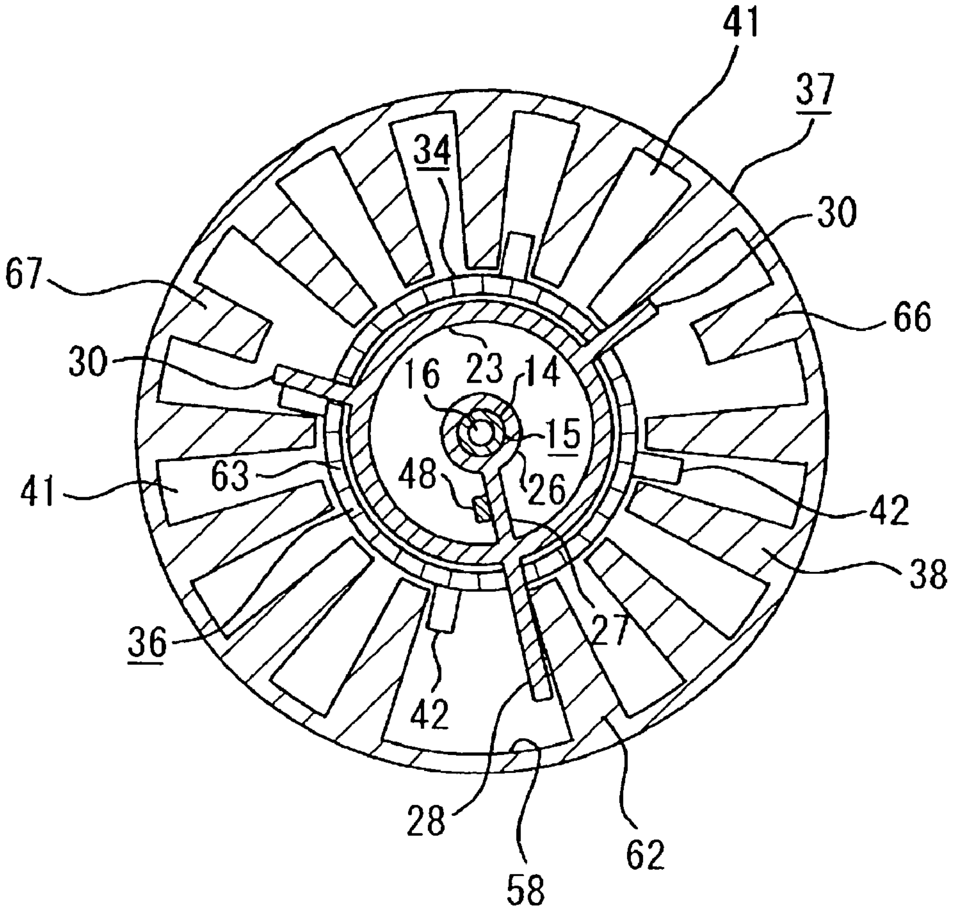
FIG. 10 is a cross section of FIG. 2 along the line A-A.

Thus, the rotating body 23 rotates together with the pushing body 45 as shown in FIG. 10, and the fitting piece 28 located on the lower end surface 63 of the sending blade 36 corresponding to the lower sleeve projection 21 crosses over the vertex 40 on a projecting side of a subsequent sending blade 36 located next to the aforementioned sending blade 36 in a proceeding direction as indicated by a dashed-dot line shown in FIG. 5, thereby being disposed at a lower end surface 63 of the subsequent sending blade 36 in a state where the side surface of the fitting piece 28 is in contact with the side surface of the first receiving blade 62 as indicated by a full line shown in FIG. 5.

Each of the fitting pieces 30 also crosses over the vertex 40 on the projecting side of the subsequent sending blade 36 in the substantially same manner, thereby being disposed at the next fitting position. In the meanwhile, as shown in FIG. 9 and FIG. 10, formation lengths of a fifth receiving blade 66 and an eleventh receiving blade 67 are set to shorter than the other receiving blades 38 in order to prevent the rotating body 23 from becoming rotatably immovable by coming in contact with the corresponding fifth receiving blade 66 and the eleventh receiving blade 67 at the time that the fitting short piece 30 crosses over the vertex 40 of the sending blade 36

The pushing body 45 can rotate in a circumferential direction independently from the annular body 34 or the rotating body 23 as described above, thereby enabling the projecting piece 48 of the pushing body 45 to rotate freely within a range such that the projecting piece 48 does not come in contact with the contact wall 27 of the rotating body 23. Therefore, the rotating body 23 rotates in a proceeding direction by positional movement of the fitting piece 28 during a pushing operation of the pushing body 45 but the pushing body 45 is formed separately from the rotating body 23, thereby not necessarily rotating in association with this rotation of the rotating body 23.

Therefore, even where the pushing body 45 is rendered to rotate in a proceeding direction somewhat in a case of performing injection by pushing the pushing projection 45, such a case is not caused, that the rotating body 23 moves between the plurality of insertion intervals 41 in association with rotation of the pushing body 45 as long as the projecting piece 48 of the pushing body 45 does not come in contact with the contact wall 27 of the rotating body 23. Furthermore, even where only the pushing body 45 is rendered to rotate in mistake in a state where the injection is not performed, such a problem can be avoided, that the fitting piece 28 positionally moves into the subsequent insertion interval 41 certainly in association with the rotation of the pushing body 45, as long as the projecting piece 48 does not come in contact with the contact wall 27, since the pushing body 45 rotates independently from the rotating body 23. Therefore, it becomes possible to certainly stabilize the whole injection amount of aerosol contents to be injected in use of one cycle.

As shown in FIG. 1, the bottom projections 50 are formed at the bottom surface 47 of the pushing body 45, thereby reducing frictional resistance which is caused between the upper surface of the annular body 34 and the bottom surface 47 of the pushing body 45 at the time of rotation of the pushing body 45, so that the pushing body 45 can be rendered to rotate more smoothly.

It becomes possible to inject again the fixed amount of aerosol contents fifteen times in total by pushing continuously the pushing body 45 after placement of the fitting piece 28 and the fitting short pieces 30 to locations for the use of the first one cycle, as described above. Therefore, the injection amount of the aerosol contents usable in a prescribed period can be limited to a prescribed amount while risks that aerosol contents are otherwise used more than the prescribed can be avoided since a special procedure is required to restart subsequent use for the next cycle after completion of the use for the first cycle, in which the pushing body 45 is manually rotated in a proceeding direction in a non-pushing state.

For example, where the head of human being is the injection target portion 64, the aerosol contents of the prescribed amount can reach the whole head of human being entirely by injections fifteen times with changing the injection location at each injection. It is to be noted that the total injection number for one cycle is limited to fifteen times in this embodiment but may be set more or less than fifteen times by adjustment of the number of the receiving blades 38 of the upper sleeve 37 and the sending blades 36 of the annular body 34 in other embodiments.

The followings can be used as the fixed amount injection valve 3 in the embodiment described above.

A-1

The fixed amount injection valve 3 used in an upside down manner, includes the lid 2 having an aluminum material coated with polyamide-imide resin paint, the housing 8 and the stem 4 made from polyoxymethylene, the stem gasket 5 made from butyl rubber, and the stem spring 65 made from stainless steel.

A-2

The fixed amount injection valve used in an upside down manner, includes the lid having an aluminum material coated with polyamide-imide resin paint, the housing 8 and the stem 4 made from polybutylene terephthalate, the stem gasket 5 made from butyl rubber, and the stem spring 65 made from stainless steel.

A-3

The fixed amount injection valve 3 used in an upside down manner, includes the lid 2 having an aluminum material laminated with polyethylene terephthalate paint, the housing 8 and the stem 4 made from polyoxymethylene, the stem gasket 5 made from butyl rubber, and the stem spring 65 made from stainless steel.

Example of a prescription for undiluted solution of the aerosol contents contained in the aerosol container 1 and used as a hair growth agent in the aforementioned embodiment can be as follows:

| (Ingredients) | (Compounding Amount) |
|---|---|
| B-1 | |
| minoxidil | 2.0 g |
| pentadecanoic acid glyceride | 0.1 g |
| tocopheryl acetate | 0.08 g |
| pantothenyl ethyl ether | 1.0 g |
| chamomile oil | 0.001 g |
| L-arginine | 0.1 g |
| capsicum tincture | 0.1 g |
| glycyrrhizinate | 0.1 g |
| 1-menthol | 0.3 g |
| menthyl lactate | 0.1 g |
| 1,3-butylene glycol | 10.0 g |
| ethanol | 60.05 g |
| citric acid | a proper amount (adjustment of the undiluted solution pH to 8) |
| purified water | a residual amount |
| Sum Total | 100 ml |
| B-2 | |
| minoxidil | 1.0 g |
| pentadecanoic acid glyceride | 1.0 g |
| tocopheryl acetate | 0.1 g |
| pantothenyl ethyl ether | 1.0 g |
| panacis japonici rhizoma extract | 2.0 ml |
| glycyrrhizinate | 0.1 g |
| 1-menthol | 0.3 g |
| 1,3-butylene glycol | 10.0 g |

-continued

| (Ingredients) | (Compounding Amount) |
|---|---|
| isopropyl alcohol | 12.0 g |
| ethanol | 55.76 g |
| lactic acid | a proper amount (adjustment of the undiluted solution pH to 8) |
| purified water | a residual amount |
| Sum Total | 100 ml |
| B-3 | |
| minoxidil | 1.0 g |
| pentadecanoic acid glyceride | 0.2 g |
| tocopheryl acetate | 0.05 g |
| pantothenyl ethyl ether | 1.0 g |
| polygonum multiflorum root tincture | 3.0 ml |
| panacis japonici rhizoma extract | 3.0 ml |
| glycyrrhizinate dipotassium | 0.1 g |
| hinokitol | 0.05 g |
| 1-menthol | 1.0 g |
| 1,3-butylene glycol | 5.0 g |
| glycerin | 5.0 g |
| ethanol | 60.05 g |
| lactic acid | a proper amount (adjustment of the undiluted solution pH to 8) |
| purified water | a residual amount |
| Sum Total | 100 ml |
| B-4 | |
| minoxidil | 3.0 g |
| tocopheryl acetate | 0.05 g |
| pantothenyl alcohol | 1.0 g |
| 1-menthol | 1.0 g |
| polyoxyethylene hydrogenated castor oil | 0.1 g |
| polyethyleneglycol400 | 5.0 g |
| 1,3-butylene glycol | 5.0 g |
| glycerin | 5.0 g |
| ethanol | 55.76 g |
| lactic acid | a proper amount (adjustment of the undiluted solution pH to 8) |
| purified water | a residual amount |
| Sum Total | 100 ml |
| B-5 | |
| minoxidil | 5.0 g |
| 1-menthol | 1.0 g |
| polyethyleneglycol400 | 10.0 g |
| ethanol | 60.05 g |
| lactic acid | a proper amount (adjustment of the undiluted solution pH to 5.4) |
| purified water | a residual amount |
| Sum Total | 100 ml |

Furthermore, the followings can be used as an aerosol content propellant in this embodiment:

C-1 dimethyl ether;

C-2 LPG; and

C-3 dimethyl ether and LPG (volume ratio is set to 1:1)

Yet further, each embodiment using the fixed amount injection valve 3, the undiluted solution of the aerosol contents, and the aerosol content propellant is shown in the following table 1.

TABLE 1

| | fixed amount injection valve | undiluted solution | propellant | filled amount undiluted solution (ml): propellant (ml) |
|---|---|---|---|---|
| First embodiment | A-1 | B-1 | C-1 | 67:33 |
| Second embodiment | A-1 | B-2 | C-2 | 85:15 |
| Third embodiment | A-1 | B-3 | C-3 | 67:33 |
| Fourth embodiment | A-1 | B-4 | C-1 | 50:50 |
| Fifth embodiment | A-1 | B-5 | C-1 | 33:67 |
| Sixth embodiment | A-2 | B-1 | C-1 | 67:33 |
| Seventh embodiment | A-2 | B-2 | C-2 | 85:15 |
| Eighth embodiment | A-2 | B-3 | C-3 | 67:33 |
| Ninth embodiment | A-2 | B-4 | C-1 | 50:50 |
| Tenth embodiment | A-2 | B-5 | C-2 | 33:67 |
| Eleventh embodiment | A-3 | B-1 | C-1 | 67:33 |
| Twelfth embodiment | A-3 | B-2 | C-2 | 85:15 |
| Thirteenth embodiment | A-3 | B-3 | C-3 | 67:33 |
| Fourteenth embodiment | A-3 | B-4 | C-1 | 50:50 |
| Fifteenth embodiment | A-3 | B-5 | C-2 | 33:67 |

What is claimed is:

1. A subdivided fixed amount distributing apparatus for attachment to an aerosol container having a fixed amount injection valve disposed within a pressurized volume of the aerosol container and having a stem slidably extending from the aerosol container, the distributing apparatus comprising:

a lower sleeve configured to be secured to a top end of the aerosol container and defining a center opening in a center thereof;

a nozzle body disposed in the center opening of the lower sleeve and formed with a nozzle bar having a lower end connectable to the stem extending from the aerosol container for delivering contents in the aerosol container, the nozzle body having a nozzle communicating with the stem;

a rotating body disposed at an upper side of the nozzle body, the rotating body having a tubular penetration bar extending from a center of the rotating body and the tubular penetration bar slidably accepting the nozzle bar, the rotating body being disposed rotatably with respect to the nozzle body and the lower sleeve;

a coil spring wound around the nozzle bar and situated between the rotating body and the nozzle body so as to bias the rotating body in an upward direction away from the nozzle body and the lower sleeve;

an annular body disposed at an upper side of the rotating body and having an annular body opening formed in a center of the annular body with the tubular penetration bar extending through the annular body opening, the annular body having sending blades with inclined sending blade surfaces circumferentially disposed on a bottom of the annular body, the inclined sending blade surfaces being inclined relative to a circumferential direction of the annular body;

a pushing body disposed at an upper side of the annular body and having a pushing body opening accepting the penetration bar, the pushing body being disposed to push the stem via the annular body, the rotating body, and the nozzle body when a user effects a pushing down operation on the pushing body to open the fixed amount injection valve disposed in the aerosol container thereby allowing ejection of entire amounts of aerosol contents, stored within the fixed amount injection valve, through the nozzle body and out the nozzle;

an upper sleeve secured to the lower sleeve at a lower end of the upper sleeve, the upper sleeve having a center opening slidably accepting the pushing body therethrough, and the upper sleeve securing between the upper sleeve and the lower sleeve in sequence the pushing body, the annular body, the rotating body, the spring, and nozzle body such that downward displacement of the pushing body by a user displaces said the annular body together with the rotating body against the bias of the spring and toward the nozzle body in a downward direction toward the aerosol container so that the rotating body engages the nozzle body to effect downward displacement of the stem via the nozzle body;

the upper sleeve having receiving blades extending downward from a top inner surface of the upper sleeve and being disposed annularly around an inner circumference of the upper sleeve and defining insertion intervals between adjacent ones of the receiving blades, the receiving blades each having a receiving blade lower end inclined surface formed as a tapered portion which is inclined relative to a circumferential direction of the upper sleeve;

said rotating body having a fitting piece projecting radially outward from an outer periphery of the rotating body such that rotation of the rotating body positions the fitting piece to align to slidably engage the receiving blade lower end inclined surfaces, to align to be insertable in the insertion intervals between the receiving blades, and such that the fitting piece is slidably engageable by the inclined sending blade surfaces of the annular body;

the rotating body and the fitting piece being so configured that downward displacement of the pushing body the user pushes the annular body downward so that the fitting piece of the rotating body is pushed by the inclined sending blade surfaces of the annular body to a position lower than the receiving blade lower end inclined surfaces of the receiving blades along with the annular body to push the stem via the rotating body and the nozzle body to enable the fixed amount of the aerosol contents to be elected, and the fitting piece being so configured that the inclined sending blades surfaces engage and rotationally displaces the fitting piece in a first rotating direction so as to rotate the rotating body a predetermined amount;

the rotating body and the fitting piece are so configured that release by the user of the downward displacement of the pushing body allows the spring biasing to move the rotating body, the annular body and the pushing body upward such that the fitting piece slidably engages one of the receiving blade lower end inclined surfaces so as to be rotationally displaced another predetermined amount in the first rotating direction and further upward movement inserts the fitting piece in one of the insertion intervals adjacent the one of the receiving blade lower end inclined surfaces such that subsequent downward displacement of the pushing body results in a further rotational displacement of the fitting piece and the rotating body in the first rotational direction by sliding engagement with a next one of the inclined sending blades surfaces, and subsequence release of downward displacement results in a further rotational displacement of the fitting piece and the rotating body by sliding engagement with a next one of the receiving blade lower end inclined surfaces thereby effecting rotation of the rotating body by the repeated downward displacement and release of the pushing body;

said lower sleeve including a lower sleeve projection extending upward from an upper end surface of the lower sleeve and positioned such that rotation of the fitting piece and the rotating body by a predetermined number of the downward displacements of the pushing body and releases thereof rotates the fitting piece into a position aligned with the lower sleeve projection such that further downward displacement of the fitting piece and the rotating body is obstructed by the lower sleeve projection engaging the fitting piece and further stem displacement and content ejection is prevented.

2. The subdivided fixed amount distributing apparatus for an aerosol container according to claim 1, wherein:

the pushing body is provided with a pushing body projecting piece extending downward from a bottom surface of the pushing body;

the rotating body has a radially offset upwardly projecting contact wall circumferentially aligned with the pushing body projecting piece; and wherein the pushing body is rotatably disposed within the upper sleeve such that rotation of the pushing body effects engagement of the pushing body projecting piece with the contact wall of the rotating body and rotational displacement of the rotating body and the fitting piece such the said obstruction of downward displacement of the fitting piece by the lower sleeve projection is releasable upon the rotation of the rotating body in association with manual rotation of the pushing body moving the fitting piece out of alignment with the lower sleeve projection.

3. The subdivided fixed amount distributing apparatus for an aerosol container according to claim 1, wherein the pushing body is formed with a pushing projection at an upper surface thereof to be placed in pressurized contact with a user to effect said downward displacement of the pushing body.

* * * * *